United States Patent
Carron et al.

(10) Patent No.: US 7,962,199 B2
(45) Date of Patent: Jun. 14, 2011

(54) METHOD AND APPARATUS FOR DETERMINATION OF BONE FRACTURE RISK USING RAMAN SPECTROSCOPY

(75) Inventors: Keith Carron, Centennial, WY (US); Mark Towler, Kilkalde (IE)

(73) Assignee: University of Wyoming, Laramie, WY (US)

( * ) Notice: Subject to any disclaimer, the term of this patent is extended or adjusted under 35 U.S.C. 154(b) by 349 days.

(21) Appl. No.: 11/994,246

(22) PCT Filed: Jun. 29, 2006

(86) PCT No.: PCT/US2006/025426
§ 371 (c)(1),
(2), (4) Date: Sep. 22, 2008

(87) PCT Pub. No.: WO2007/005540
PCT Pub. Date: Jan. 11, 2007

(65) Prior Publication Data
US 2009/0012403 A1     Jan. 8, 2009

Related U.S. Application Data

(60) Provisional application No. 60/695,629, filed on Jun. 30, 2005, provisional application No. 60/725,206, filed on Oct. 11, 2005.

(51) Int. Cl.
*A61B 5/05* (2006.01)
(52) U.S. Cl. ........................ 600/473; 382/128
(58) Field of Classification Search .................. 600/310, 600/473–475; 356/300, 301–303, 928, 952
See application file for complete search history.

(56) References Cited

U.S. PATENT DOCUMENTS
2002/0002336 A1 * 1/2002 Marchitto et al. ............ 600/473

FOREIGN PATENT DOCUMENTS
WO    WO2007/005540 A2    1/2007

OTHER PUBLICATIONS

I. Pillay, M.R.C.P., D. Lyons, M.D., F.R.C.P., M.J. German, Ph.D., N.S. Lawson, Ph.D., H.M. Pollock, PH. J. Saunders, P.H.D., S. Chowdhury, B.SC., P. Moran, B.SC., and M.R. Towler, Ph.D., The Use of Fingernails as a Means of Assessing Bone Health: A Pilot Study, Journal of Women's Health, vol. 14, No. 4, 2005, Mary Ann Liebert, Inc., pp. 339-344, England.

(Continued)

*Primary Examiner* — Brian Casler
*Assistant Examiner* — Parikha S Mehta
(74) *Attorney, Agent, or Firm* — Kent A. Herink; Emily E. Harris

(57) ABSTRACT

A method is disclosed for analyzing keratinized tissue, particularly fingernails, of a subject to diagnose osteoporosis and bone fracture risk. A Raman spectrum of a sample of keratinized tissue is generated. Broad spectral background features of the spectrum are removed, preferably by using Fourier transform analysis. Peak heights of Raman features of interest, particularly the S—S bond of cystine, are measured. These peak height measurements are normalized using reference peak heights of Raman features that are invariant between normal and osteoporotic subjects, such as the $CH_2$ bending peak.

6 Claims, 8 Drawing Sheets

OTHER PUBLICATIONS

P. Moran, M.R. Towler, S. Chowdhury, J. Saunders, M.J. German, N.S. Lawson, H.M. Pollock, I. Pillay & D. Lyons, Preliminary Work on the Development of a Novel Detection Method for Osteoporosis, pp. 1-14, Ireland.

Sonja Wessel, Monika Gniadecka, Gregor B.E. Jemec, Hans Christian Wulf, Hydration of human nails investigated by NIR-FT-Raman spectroscopy, 1999 Elsevier Science B.V., pp. 210-216, Denmark.

W. Akhtar, H.G.M. Edwards, Fourier-transform Raman spectroscopy of mammalian and avian kerototic biopolymers, 1997 Elesvier Science B.V., pp. 81-90, United Kingdom.

Reference Summary, X-Plain Bone Densitometry, 1995-2004, The Patient Education Institute, Inc., www.X-Plain.com, pp. 1-2.

* cited by examiner

METHOD AND APPARATUS FOR DETERMINATION OF BONE FRACTURE RISK USING RAMAN SPECTROSCOPY

This application claims priority to U.S. Patent Application Ser. No. 60/695,629, filed Jun. 30, 2005 and U.S. Patent Application Ser. No. 60/725,206, filed Oct. 11, 2005.

BACKGROUND OF THE INVENTION

The invention relates generally to methods for detecting the risk of bone fracture and, more specifically, to a method for determining the existence of low bone quality using Raman spectroscopy.

Osteoporosis is a condition that features loss of the normal density of bone and leads to abnormally porous bone. Osteoporosis affects over 44 million Americans and over one-half of these are women. The exact cause of osteoporosis is unknown. Since bones are composed of a mixture of an organic phase, primarily collagen, and an inorganic phase, primarily calcium phosphate, a prevailing thought has been that calcium deficiency leads to osteoporosis. The propensity of osteoporosis in women supports this conclusion since they often lose calcium from lactation and throughout menopause. Osteoporosis is however a poor predictor of bone fracture the clinical endpoint. The need for Bone Quality based assessments that may have improved prediction capability is well known. The current diagnostic tool, the bone mineral density scan, measures the absorption of X-rays by the calcium content in bone tissue. Accordingly, the diagnostic value of the bone density X-ray scan (DEXA scan) relies on the validity of the calcium deficiency theory of osteoporosis. Unfortunately, patients who suffer osteoporotic fractures often have normal bone density, because it is the organic phase, as well as the mineral phase, that is affected.

Bone densitometry is an involved and expensive method to measure bone density. It also has a large amount of uncertainty. The Mayo Clinic offers the following views on bone densitometry: "Bone density testing is a valuable tool in the diagnosis of osteoporosis and is a fairly accurate predictor of fracture risk. Significant differences in the various testing methods do exist, however. Central devices are more accurate, but cost significantly more than peripheral devices. The U.S. government has ordered Medicare to pay for bone density testing in the following instances: (1) If you're postmenopausal and at risk of osteoporosis; (2) if you have primary hyperparathyroidism; (3) if you have certain spinal abnormalities that might indicate a fracture; (4) if you're on long-term corticosteroid therapy, such as prednisone; or (5) if your doctor wants to assess your response to osteoporosis medications," www.mayoclinic.com/invoke.cfm?id=WO00024

Much of the "fairly accurate predictor" language may stem from the belief that osteoporosis is a disease of the calcium content of bones. It is now, however, fairly well accepted that bone fracture risk can derive from protein problems. Bone matrix is composed of collagenous and non-collagenous bone proteins. Collagen synthesis, secretion and deposition are coordinated with that of the other matrix proteins. Cystine residues with disulphide bonding are a feature of all non-collagenous bone proteins. It is thought that the placement of cystine residues within structural proteins and consequent disulphide bonding might result in structures with varied activities. Although the mechanism of bone formation is not yet defined, the need for cystine and for some, sulfation of the bone proteins is common to all proposed mechanisms. Moreover, there is an in vivo exchange between inorganic and organic sulfate chiefly due to the synthesis and breakdown of sulfated glycosaminoglycans, which form the ground substance of bone matrix. Bone fragility may result from a disturbance, to variable degree, of these collagenous and non-collagenous bone proteins.

A publication by Akhtar and Edwards (Akhtar, W. and Edwards, H. G. M. Fourier-transform Raman spectroscopy of mammalian and avian keratotic biopolymers, Spectrochimica Acta Part A, 53, (1997) p. 81-89) outlines how mammal and avian human nails and animal beaks, quills, and claws vary in the width of the S—S band of cystine. They attribute these differences to the conformations of the S—S bond. For example, 510 $cm^{-1}$ corresponds to gauche-gauche-gauche, 525 $cm^{-1}$ corresponds to gauche-gauche-trans, and 540 $cm^{-1}$ corresponds to trans-gauche-trans. While each of these bands can be assigned in most circumstances they are unresolved peaks or represent an unsymmetric single feature. Later Edwards used these observation to determine the health of mummified humans and birds (Edwards, A. G. M, Gniadecka, M, Ptersen. S., Hansen, J., Nielson, O., Christensen, D., Wulf, H. NIR-FT Raman spectroscopy as a diagnostic probe for mummified skin and nails, Vibrational Spectroscopy, 28, 2002, p. 3-15).

An even early publication Schrader, et al., discusses the general value of near-infrared Fourier transform Raman spectroscopy in attempting to diagnose medical conditions. This publication showed many different applications of Raman spectroscopy for medical diagnoses, but relevant to this application, they showed the spectrum of a fingernail and discussed the large S—S stretch from cystine and discussed spectrum could indicated metabolic disorders.

Recently a group at the University of Limerick found a strong correlation between the Raman spectra of fingernail protein and osteoporosis. Moran, P., et al. Preliminary Work on the Development of a Novel Detection Method for Osteoporosis (Submitted); PCT Application No. WO 2005122893. The specific observation by the Limerick group was that the disulfide Raman feature from the amino acid cystine appears to broaden in patients with osteoporosis and increased bone fracture risk. This indicates that calcium may not be the direct culprit in osteoporosis and bone fractures and it may be a disease related to the protein component of bone material.

The problem with Limerick's approach is that it is very difficult to measure the width (more specifically the "full width at half maximum") of a peak. It is also unclear exactly what the origin of the bandwidth change is. It is possible that it is due to different conformations of the cystine in the collagen material. This will lead to more than one peak in the Raman spectrum and may manifest itself through a peak broadening.

The intensity of a Raman peak is directly related to the amount of material. If the amount of cystine is constant in healthy and osteoporotic collagen then the increased spectral width of the band should lead to a decrease in the intensity of the peal. This can be difficult to measure since natural materials such as fingernails have significant fluorescent backgrounds.

SUMMARY OF THE INVENTION

In preferred embodiments, the present invention consists of a method of detecting bone fracture risk based on bone quality in a subject by generating a Raman spectrum of a sample of keratinized tissue, such as hair, skin, or nails, of the subject. The broad spectral background features of the spectrum are removed by a mathematical procedure, preferably using a digital computer. The height of a peak or peaks of interest, preferably including a peak representative of cystine, is measured. The height of the peak, or peaks, of interest is then normalized using an invariant reference peak height to account for the thickness of the subject's keratinized tissue sample.

The mathematical procedure preferably includes performing a Fourier transform on the sample spectrum, and removing the high frequency components from the sample spectrum. An inverse Fourier transform is performed on the modified, transformed spectrum to produce a spectrum without Raman features. The procedure then subtracts the background spectrum from the sample spectrum to produce a fairly flat spectrum, but with the Raman features enhanced.

The present invention can be used as a diagnostic aid for assessing the risk of disease such as osteoporosis and the corresponding bone fracture risk. The Raman imaging technique of the invention provides a non-invasive and rapid determination of the risk of osteoporosis and bone fracture risk in live subjects. The present invention thus offers valuable diagnostic information applicable to large populations that may help in assessing an individual's risk of having bone fracture, and in determining protocols for prevention of the same. In a preferred embodiment of the present invention, the method is automated and carried out in a single instrument without the need for an operator. Accordingly, a lay subject wishing to be tested for loss of bone strength can place the keratinized tissue sample, either removed from the subject or still resident on the subject, into the instrument and the instrument will automatically carry out the method and provide an output to the subject indicative of the bone health of the subject. Alternatively the instrument may be used by a health care practitioner to analyze samples of keratinized tissue of a subject under the care or treatment of the health care professional.

These and other advantages and features of the present invention will become more fully apparent from this disclosure, the associated drawings, and the appended claims, or may be learned by the practice of the invention as set forth herein.

DETAILED DESCRIPTION OF PREFERRED EMBODIMENTS

Figure 8:
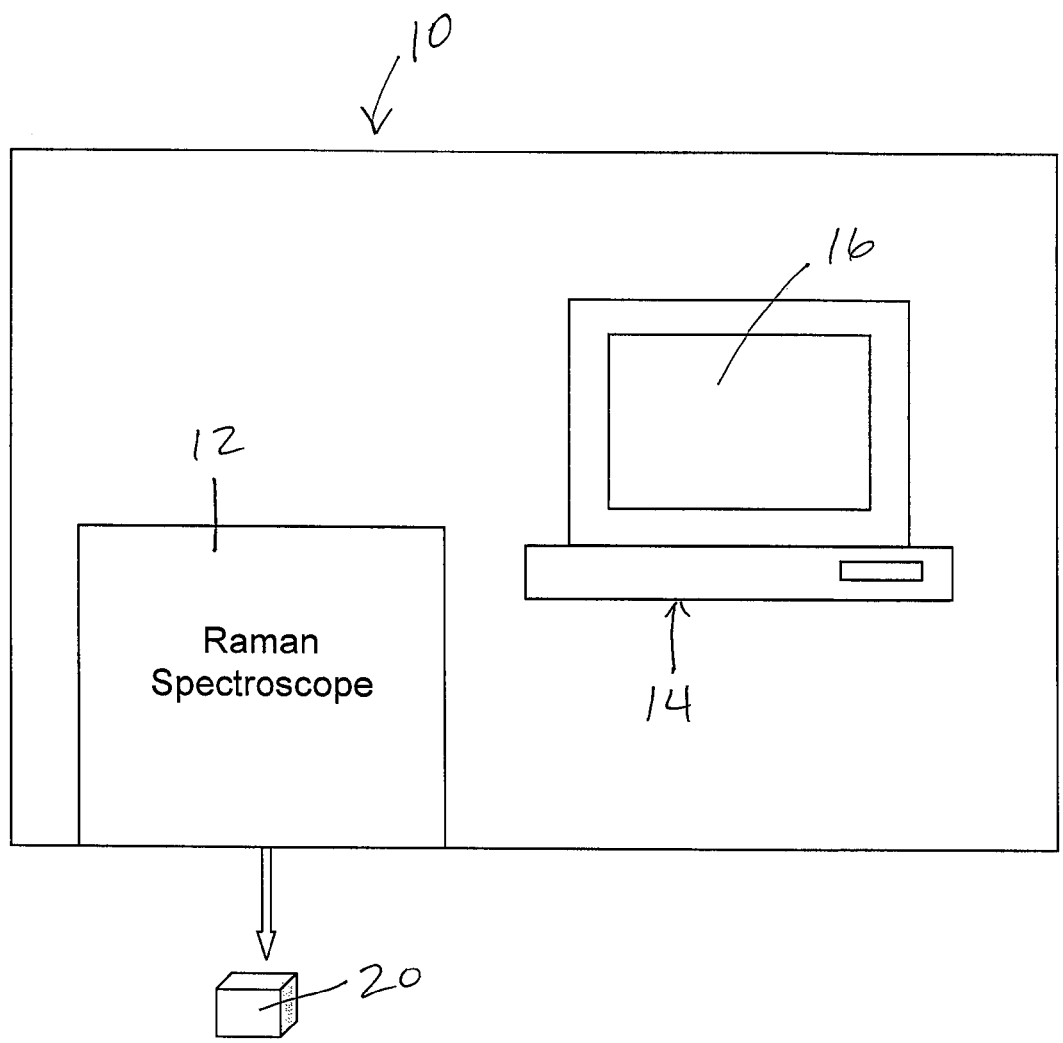
FIG. 8 is, a schematic diagram of apparatus of a preferred embodiment of the invention.

Raman spectroscopy is the measurement of the wavelength and intensity of inelastically scattered light from molecules. The Raman scattered light occurs at wavelengths that are shifted from the incident light by the energies of molecular vibrations. The mechanism of Raman scattering is different from that of infrared (IR) absorption, and Raman and IR spectra provide complementary information. Raman spectroscopy is commonly used in chemistry, since vibrational information is very specific for the chemical bonds in molecules. It therefore provides a fingerprint by which the molecule can be identified. Typical applications are in structure determination, multi-component qualitative analysis, and quantitative analysis. An apparatus for performing Raman spectroscopy in the detection of carotenoids in the macular tissue of a subject is described in U.S. Pat. No. 7,039,452, which is incorporated herein by this reference. An apparatus for performing Raman spectroscopy in the detection of bone health using the width of the peaks us described n PCT Application No. WO 2005122893, which is incorporated herein by this reference. As illustrated in FIG. 8, an instrument 10 of a preferred embodiment of the present invention includes a Raman spectroscope 12, and a digital computer 14 having a display 16 by which information from the digital computer 14 may be output in human readable form. A sample of keratinized tissue 20 is shown in range for scanning by the Raman spectroscope 12.

The present invention relates to a spectroscopic method that solves the difficulties of measuring the intensity of a Raman feature in order to provide an assay of the degree of bone fracture risk in a subject. Included in the Raman spectra of keratinized tissue, specifically human fingernails, are peaks that provide information about the sulfur bonding in the fingernails. The relative intensities of the carbon sulfide bond (C—S) and disulfide bond (S—S) stretching vibrations are indicative of the amount of sulfur present in the fingernails and also provide information about the structural configuration of the S—S bond. (Moran, et al., supra.) In a Raman spectrum, the disulfide peak appears at about $510\ cm^{-1}$ and the carbon sulfide bond peak appears at about $645\ cm^{-1}$. Raman spectra of fingernails also contain information not associated with sulfur content or bonding, for example, the methylene ($CH_2$) deformation band at about $1450\ cm^{-1}$ and a strong band at about $1000\ cm^{-1}$ corresponding to the C—C stretching vibration of the aromatic ring in the phenylalanine side chain. These bands are not expected to change between normal subjects and those that have an increased bone fracture risk and accordingly are useful as reference bands.

The process involves two steps. First the broad spectral background that varies from sample to sample is removed by a mathematical procedure. This procedure takes the sample spectrum, performs a Fourier transform, and removes the high frequency components from the sample spectrum. An inverse Fourier transform is performed on the modified, transformed spectrum to produce a spectrum without Raman features. The process then subtracts the background spectrum from the sample spectrum. This produces a fairly flat spectrum, but with the Raman features enhanced. Next the Raman features of interest are selected and measured.

The data generated from the spectra are analyzed, preferably using a computer or other data processing device, such as a personal computer. The detected light is converted by optical detection device into a signal which is transmitted to the computer for processing the signal data. For example, the signal data can be processed with software that produces an output image of the Raman signal levels received by an imaging means, such as a digital camera, with the image representing the Raman spectrum of the sample. The output device can be used to display or print the Raman image. For example, the image can be displayed on a visual display monitor such as a computer monitor, or sent to a printer connected to computer for printing the image.

Figure 1:
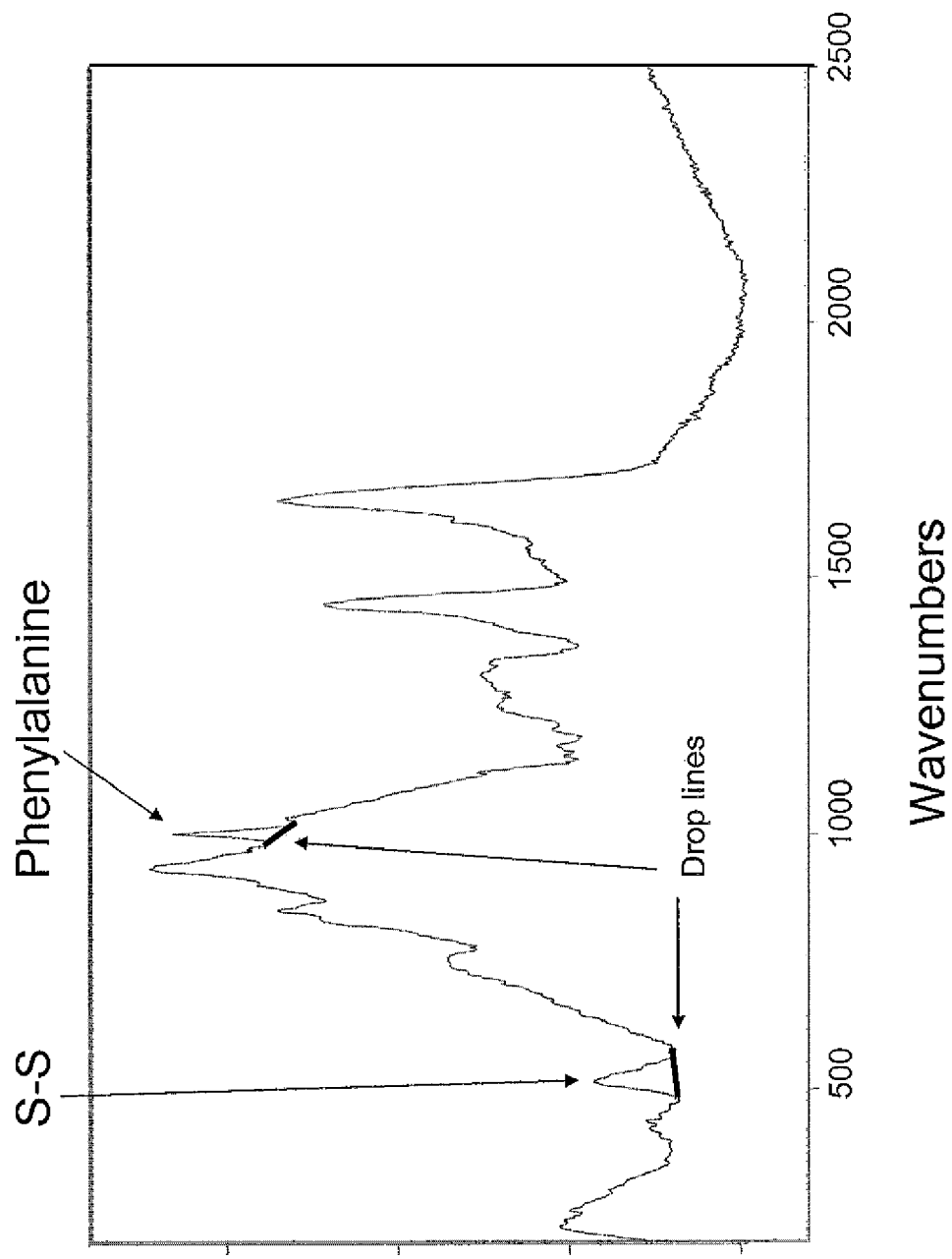
FIG. 1 is a graphical representation of a Raman spectrum of a fingernail sample in which the "dropline" method has been used to find the peak height of the disulfide (S—S) stretching vibration and a ring stretching vibration associated with phenylalanine.
Figure 2:
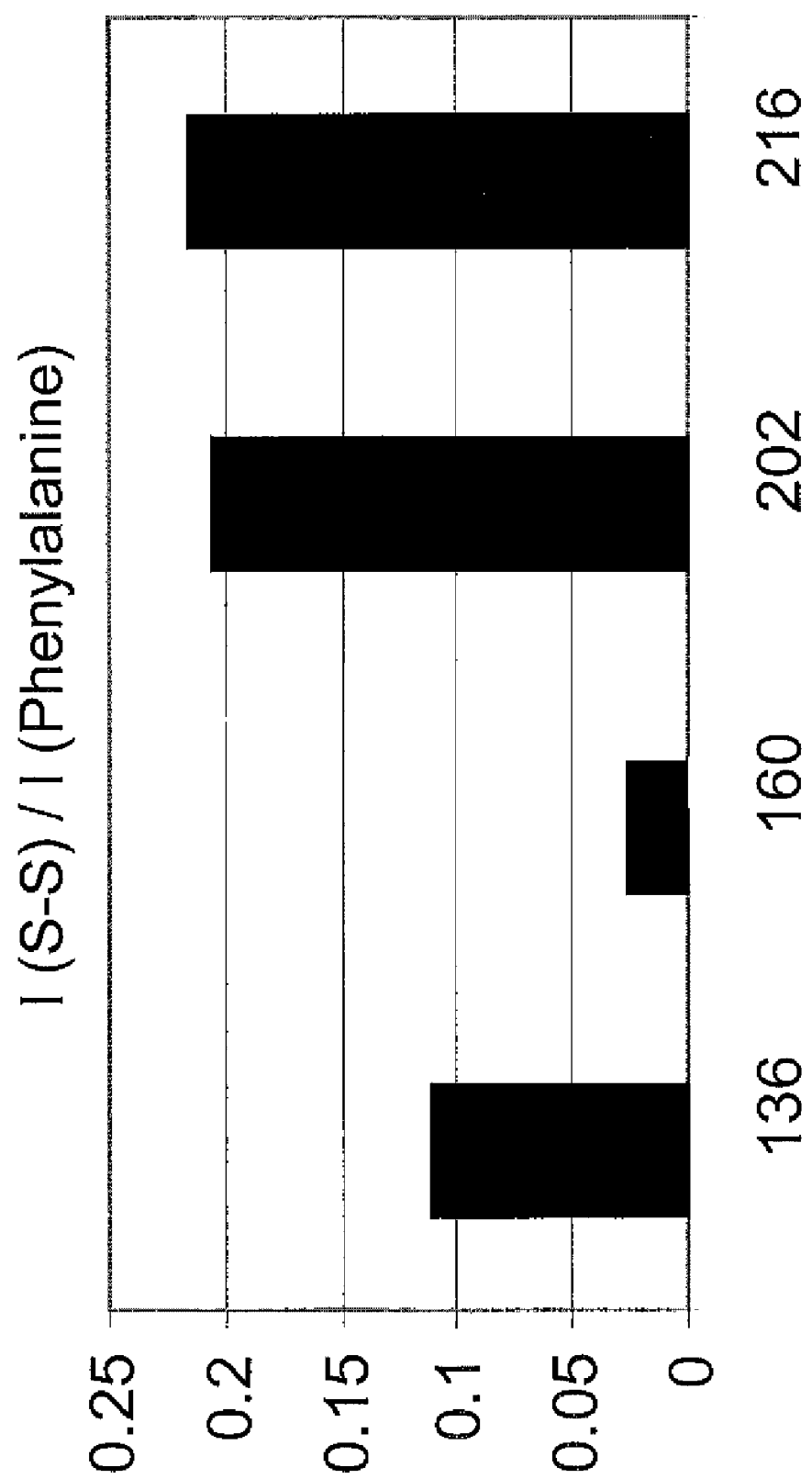
FIG. 2 is a chart of the ratios of peak heights found in the four spectra of FIG. 7 using GRAMS™ software as in FIG. 1.
Figure 3:
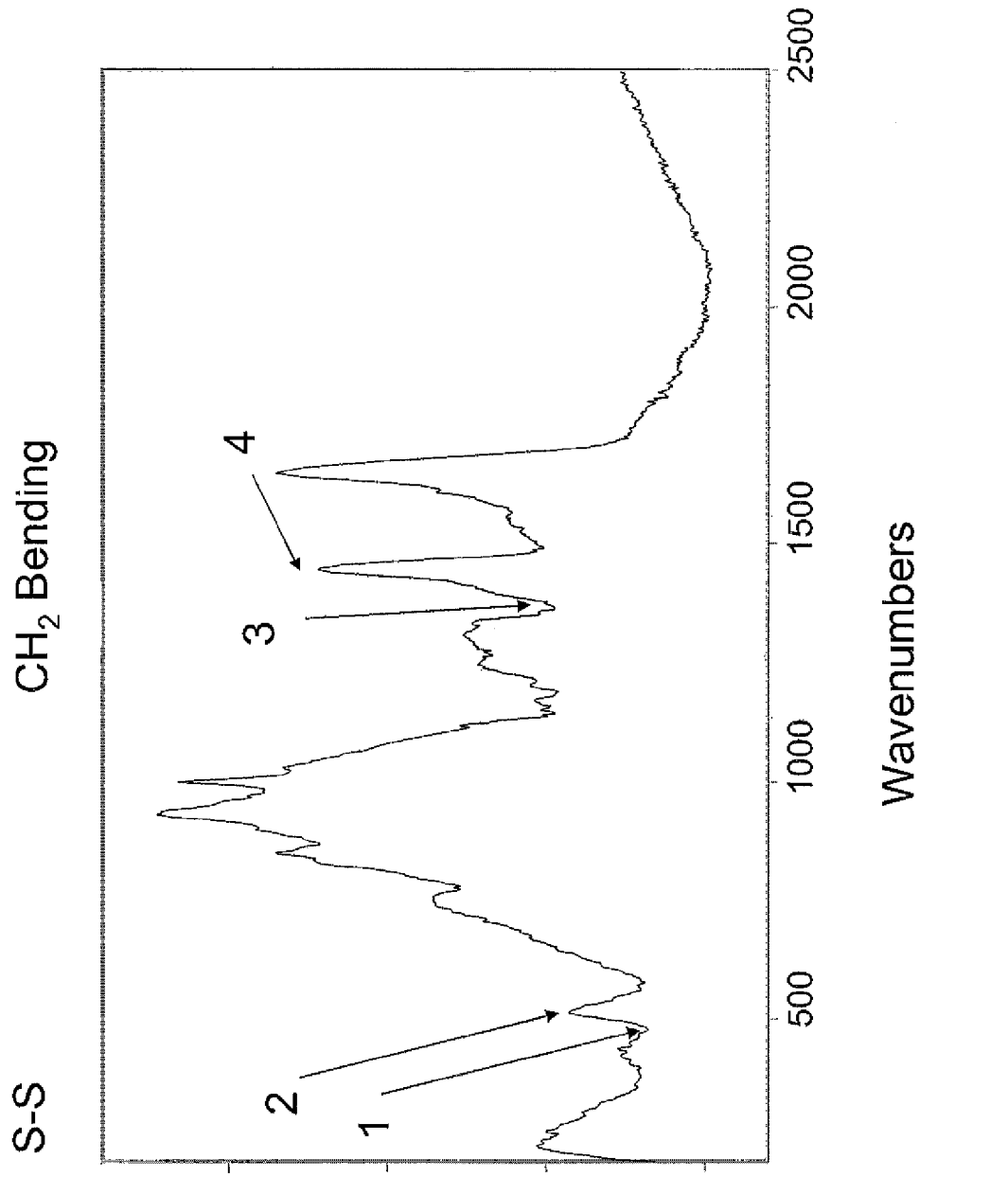
FIG. 3 is a graphical representation of a Raman spectrum of a fingernail sample wherein four points for the location of the minimum and maximum of the S—S and $CH_2$ bending peaks.
Figure 4:
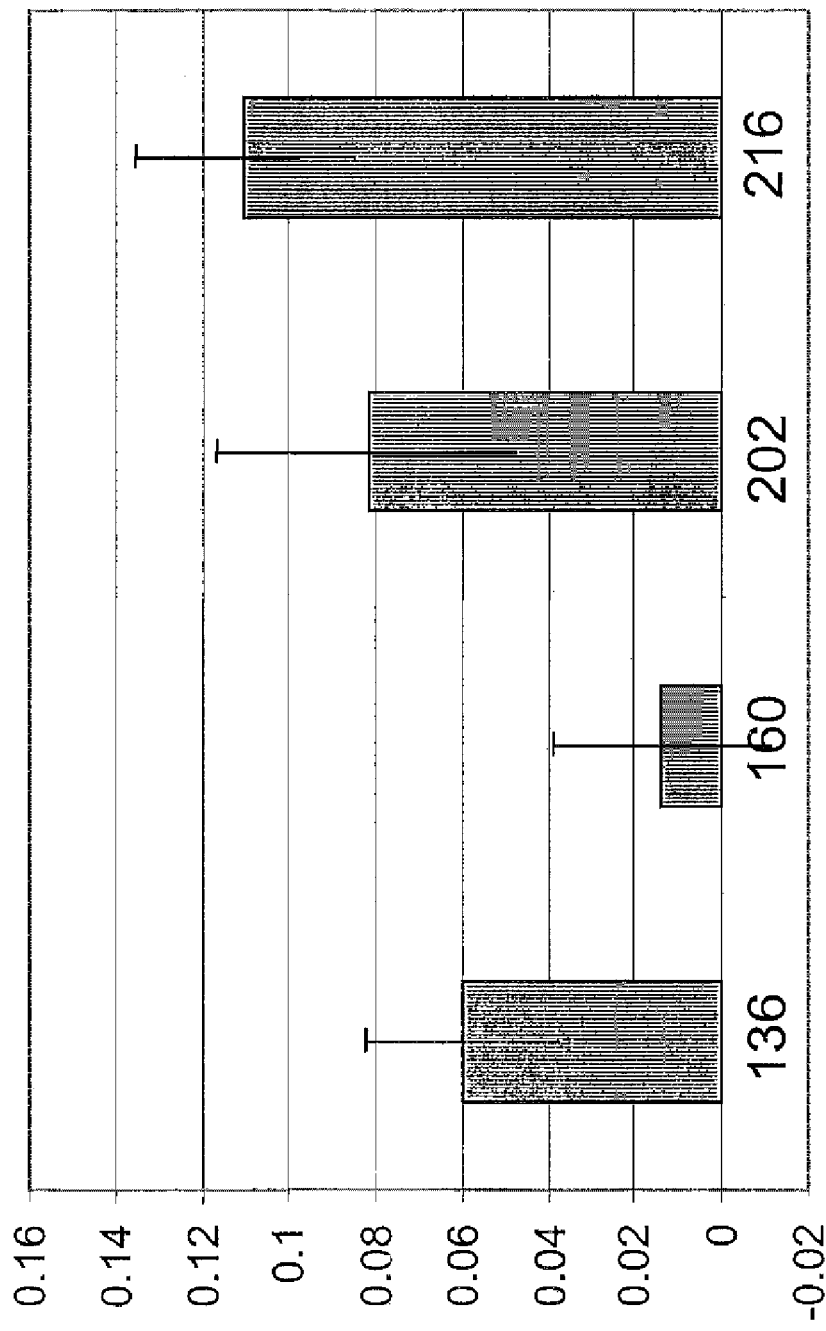
FIG. 4 is a chart of the ratios of the maxima/minima differences for the peaks of FIG. 7 averaged over five samples using the method of FIG. 3.

One method uses an external program, for example the GRAMS™ software of the Thermo Electron Corporation, MA, to produce a "dropline" to find the peak height (FIG. 1) relative to the background. This procedure does not lend itself to automation and tends to be subjective. FIG. 2 is a chart of the ratios of peak heights found in the spectra of four subjects (FIG. 7) using the method of FIG. 1. A second method uses a known spectrum and selects four points for the minimum and maximum of two peaks of interest (FIG. 3). The points 1-4 are used to find the baseline of the cystine peak, the top of the cystine peak, the baseline of the reference peak, and the top of the reference peak, respectively. FIG. 4 is a chart of the ratio of peak heights found in the spectra of four subjects (FIG. 7) using the method of FIG. 3.

The results show that most of the peaks can be used as a reference to normalize against variability in the absolute signal to make it independent of the fingernail/toenail thickness. The data provided in the figures uses the phenylalanine band near 1000 wavenumbers and the $CH_2$ peak near 1350 wavenumbers. Since the thickness, opacity, and hydration will vary between subjects and the absolute intensity of the Raman spectrum will vary with nail thickness there is a need to normalize to an internal standard. The reference bands described above appear to be invariant between subjects.

Figure 5:
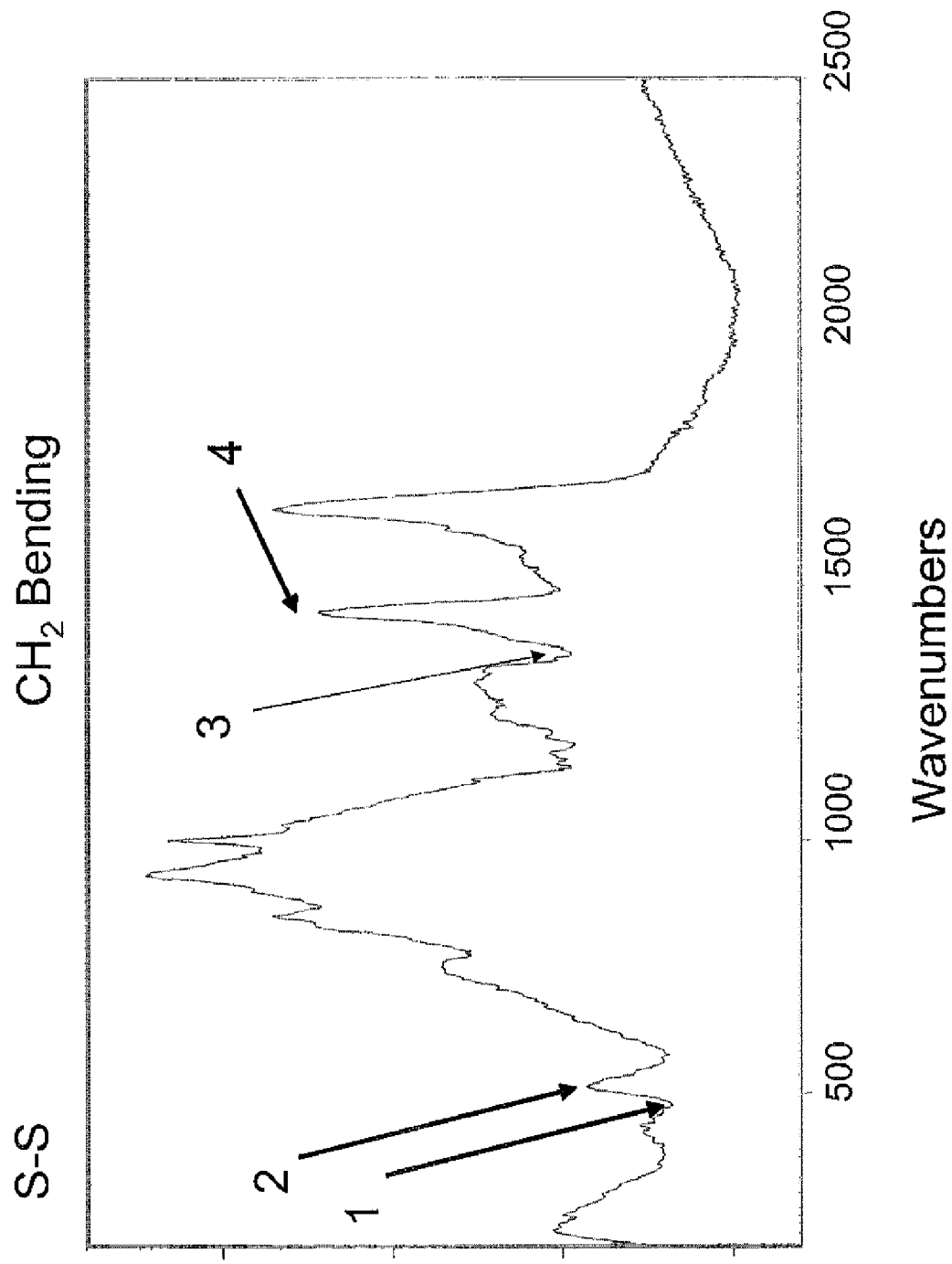
FIG. 5 is a graphical representation of a Raman spectrum of a fingernail sample wherein the data array of the Raman features of interest are searched to find the maximum (top of the peak) and the minimum (baseline) of each peak.
Figure 6:
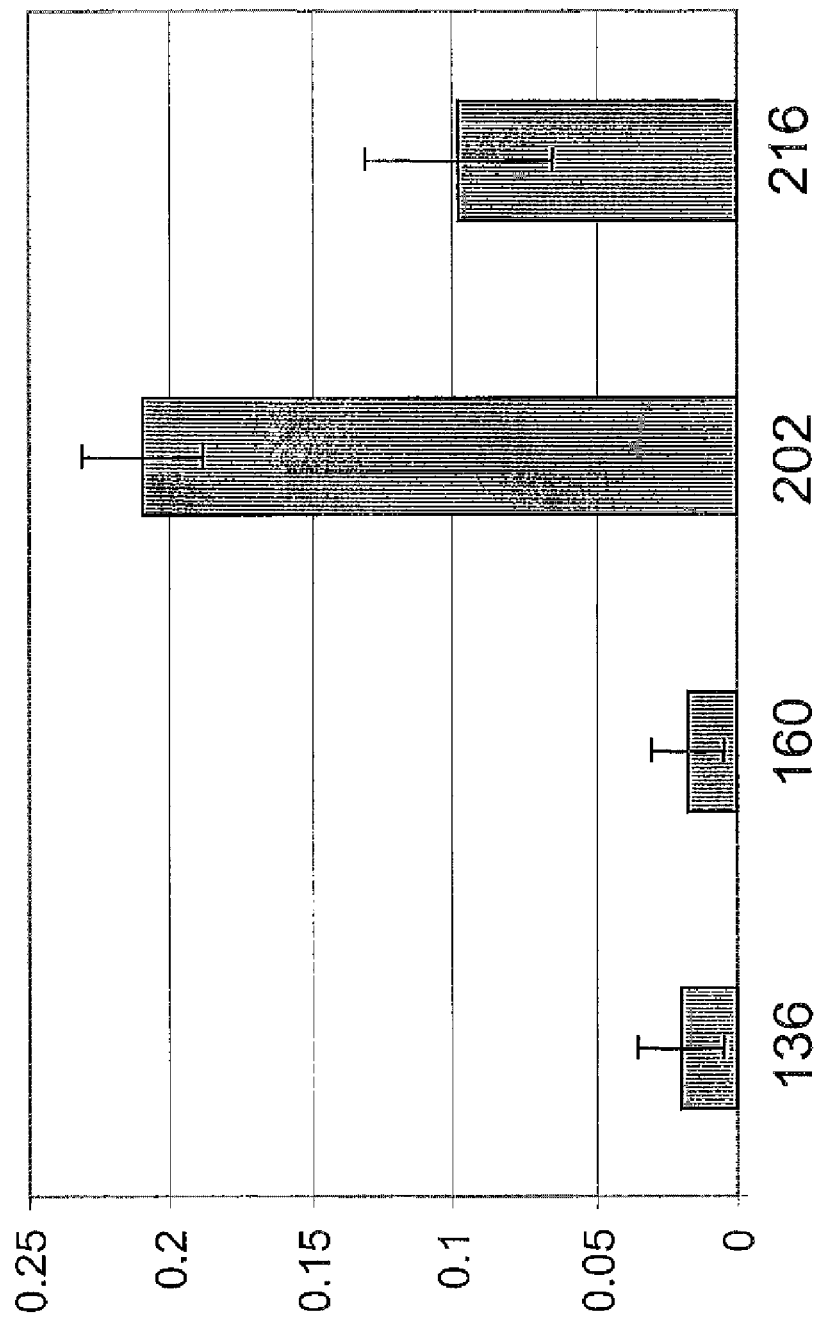
FIG. 6 is a chart of the ratios of peak heights taken from FIG. 7 using the method of FIG. 5.

The preferred method for the analysis is to choose a spectral range that includes the Raman feature and its local minima on both sides. The data array is searched to find the maximum (top of the peak) and the minimum (baseline) (FIG. 5). These are subtracted to produce the peak height as described above. The advantage of this approach is that it accounts for variations in the peak locations between samples. This produced the most accurate and precise measurements. FIG. 6 is a chart of the ratio of peak heights found in the spectra of four subjects (FIG. 7) using the method of FIG. 5. The improvement arises from better corrections for variations between nails. Method 1, the dropline method, is too subjective to produce meaningful results, Method 2 is not subjective as it uses the same points on the plot every time. However, Method 2 suffers from variations in the nails spectrum due to non-osteoporotic interferences. Method 3, allows the device to automatically find the minimum and maximum around a peak to eliminate the affect of non-osteoporotic interferences. This improvement results in a better determination of the baseline due to variations in the samples and fluorescence removal. Assuming that the change in the cystine peak is due to introduction of new conformations in the osteoporotic subjects, then this method, which finds the peak location and measures its height, will be more consistent than a method that just uses the same point every time.

Figure 7:
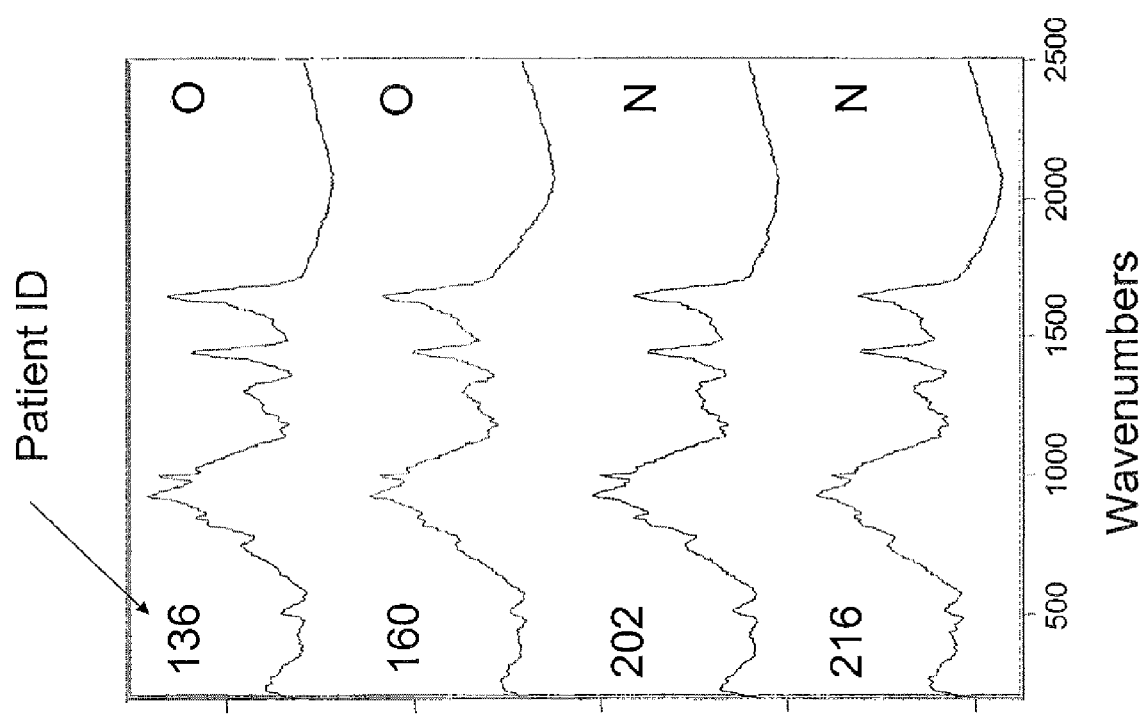
FIG. 7 are Raman spectra of fingernail samples taken from two normal subjects and two osteoporotic subjects.

FIG. 7 allows a visual comparison of the changes in the Raman spectra of two fingernail samples taken from normal subjects and two fingernail samples taken from osteoporotic subjects. Two nail clippings were taken from each subject from the free edge of the nail plate and stored in sealed specimen jars prior to analysis. Raman spectroscopy (Inspector Raman Instrument, Delta Nu, Wyoming, USA) was performed on the underside of the fingernail. Excitation was by HeNe laser operating at 633 nm. Spectra were recorded (400 $cm^{-1}$ to 1800 $cm^{-1}$) by securing the nail to the analysis port and performing ten scans, to improve the signal-to-noise ratio, each with a laser exposure time of 5 seconds. To evaluate the intensity of the S—S bonding in the sample the stretching vibration of the disulphide bond (S—S) at 510 $cm^{-1}$ was measured relative to the methylene ($CH_2$) deformation band at 1450 $cm^{-1}$ (FIG. 1). Normalising the S—S peak to the $CH_2$ peak addressed concerns regarding variable nail thickness. The average of ten scans was taken as one determination. Two determinations were performed upon each of the two nails. The result was recorded as the mean (S—S) peak height of the four readings. It would be very difficult to visually distinguish between the normal and osteoporotic patients using the Raman spectra of FIG. 7 without the analysis of the present invention.

In a preferred embodiment of the present invention, the Raman spectroscope, digital computer and output means are incorporated into a single instrument and the method of the present invention is automated so that it may be carried out using the stand-alone instrument without the assistance of a trained spectroscopist. Accordingly, the instrument could be placed in a public location, such as a drug store, where lay customers could use the instrument to measure samples (either removed or in situ) of their keratinized tissue and the instrument would automatically provide output, preferably on a display screen and on a printed form, of the bone health status of the subject, e.g., normal, osteopenic, or osteoporotic. Such instruments could also be adapted for use by health care practitioners for the testing of subjects under their care. In such instruments, it is preferred that the output provide a T-score corresponding to the T-score currently reported when bone mass or strength is measured using the prior art X-ray method of analysis.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:

1. A method of analyzing keratinized tissue of a subject to diagnose osteoporosis and bone fracture risk, comprising the steps of:
    (a) generating a Raman spectrum of a keratinized tissue sample using a Raman spectroscope, said spectrum including at least a peak of a measureable height representative of disulfide bonds and a peak of a measureable height representative of cystine;
    (b) removing broad spectral background features from the spectrum;
    (c) measuring the peak height of the peak representative of disulfide bonds; and
    (d) normalizing the cystine peak height using an invariant reference peak height.

2. A method as defined in claim 1, wherein the step of removing the broad spectral background features comprises:
    (a) performing a Fourier transform on the spectrum;
    (b) removing high frequency components to produce a modified transformed spectrum;
    (c) performing an inverse Fourier transform on the modified transformed spectrum to produce a modified spectrum, and (d) subtracting the modified spectrum from the original spectrum.

3. A method as defined in claim 1, wherein the step of measuring peak height comprises identifying peak maxima and baseline from a data array associated with the spectrum independent of a standard reference location.

4. A method as defined in claim 1, wherein the keratinized sample is selected from the group consisting of hair, skin and nails.

5. A method as defined in claim 1, wherein the sample resides in a live subject.

6. A stand-alone instrument for proving information about a risk of bone fracture of a subject, comprising a Raman spectroscope, a digital computer configured to receive and analyze spectra from the spectroscope and provides information about the bone fracture risk of the subject, and means for generating an output of the information from the digital computer in human readable form, and wherein the instrument is configured to carry out the method as defined in claim 1 upon the placement of a sample of keratinized tissue of the subject within scanning range of the instrument.

* * * * *